United States Patent
Imperante et al.

(10) Patent No.: US 6,794,524 B1
(45) Date of Patent: Sep. 21, 2004

(54) ESTER BASED PHOSPHOBETAINE COMPOUNDS

(75) Inventors: John Imperante, Somerville, NJ (US); Anthony J. O'Lenick, Jr., Dacula, NJ (US)

(73) Assignee: Phoenix Research Corporation, Somerville, NJ (US)

( * ) Notice: Subject to any disclaimer, the term of this patent is extended or adjusted under 35 U.S.C. 154(b) by 51 days.

(21) Appl. No.: 10/642,562

(22) Filed: Aug. 18, 2003

(51) Int. Cl.[7] .................................................. C07F 9/02
(52) U.S. Cl. ........................ 554/79; 564/293; 564/294
(58) Field of Search ........................... 524/79, 293, 294

(56) References Cited

U.S. PATENT DOCUMENTS 6,180,806 B1    1/2001   O'Lenick et al.
6,331,293 B1    12/2001  Smith et al.

*Primary Examiner*—Deborah D. Carr

(57) ABSTRACT

The invention relates to a series of novel ester containing phosphobetaine compounds, which are exceptional surface active agents that provide outstanding foam and are very mild to the hair and skin, in addition because of the presence of the ester linkage these materials are not persistent in the aquatic environment. This lack of persistence in the aquatic environment makes these materials greener and environmentally friendly than other non-ester containing compounds. The compounds, because they contain a pendant ionizable phosphate group and a quaternary amine compound are amphoteric surfactants that is they contain both a positive and negative charge in the same molecule. This combination of properties makes these polymers ideally suited for use in personal care applications.

19 Claims, No Drawings

ESTER BASED PHOSPHOBETAINE COMPOUNDS

BACKGROUND OF THE INVENTION

1. Field of Invention

The present invention relates to a series of novel ester containing phosphobetaine compounds which are exceptional surface active agents that provide outstanding foam and are very mild to the hair and skin, and are not persistent in the aquatic environment. The compounds, because they contain a pendant ionizable phosphate group and a quaternary amine compound are amphoteric surfactants that is they contain both a positive and negative charge in the same molecule. This combination of properties makes these polymers ideally suited for use in personal care applications.

The compounds of the present invention are based upon raw materials which are prepared by the reaction of a polyoxyalkylene containing ester with a phosphating reagent then by reaction of this intermediate with an epoxy quat intermediate.

The technology used to produce the phosphobetaine compounds of the present invention is very flexible and allows us to prepare performance tailored molecules for specific applications.

2. Description f the Arts and Practices

Fatty phosphobetaine compounds have been known since 1974. There are several patents, which have issued on this topic.

U.S. Pat. Nos. 3,856,893 and 3,928,509 both issued to Diery disclose the basic technology used to make phosphobetaine compounds.

Later, amido and imidazoline based phosphobetaine compounds were patented in U.S. Pat. No. 4,209,449 issued in 1980 to Mayhew and O'Lenick. This patent teaches that phosphate quats can be prepared by the reaction of a phosphate salt, three equivalents of epichlorohydrin and in a subsequent step, three equivalents of a tertiary amine.

U.S. Pat. No. 4,215,064 issued in 1980 to Lindemann et al teaches the basic technology that is used for the preparation of amido and imidazoline based phosphobetaine compounds. These compounds can be prepared by the reaction of a phosphate salt, one equivalent of epichlorohydrin and one equivalent of a tertiary amine.

U.S. Pat. No. 4,243,602 issued in 1981 to O'Lenick and Mayhew teaches the basic technology that is used for the preparation of phosphobetaine compounds based upon phosphorous acid salts. These compounds can be prepared by the reaction of a phosphorous acid salt, one equivalent of epichlorohydrin and one equivalent of a tertiary amine.

U.S. Pat. No. 4,261,911 issued in 1981 to Lindemann et al teaches the utilization of phosphobetaine compounds based upon phosphorous acid. These compounds are useful as surfactants.

U.S. Pat. No. 4,283,542 issued in 1981 to O'Lenick and Mayhew teaches the process technology used for the preparation of phosphobetaine compounds. These compounds can be prepared by the reaction of a phosphate salt, one equivalent of epichlorohydrin and one equivalent of a tertiary amine.

U.S. Pat. No. 4,336,386 issued in 1982 to O'Lenick and Mayhew teaches the technology for the preparation of imidazoline-derived phosphobetaine compounds based upon phosphorous acid salts. These compounds can be prepared by the reaction of a phosphorous acid salt, one equivalent of epichlorohydrin and one equivalent of an imidazoline.

U.S. Pat. No. 4,503,002, which is related to U.S. Pat. No. 4,209,449 issued in 1985 to Mayhew and O'Lenick teach that phosphate quats can be prepared by the reaction of a phosphate salt, three equivalents of epichlorohydrin and three equivalents of a tertiary amine.

U.S. Pat. No. 6,180,806 issued in 2001 to O'Lenick and Imperante disclose glyceryl phosphate quats.

Despite the fact that there was significant patenting of phosphobetaine compounds based upon phosphoric acid salts, phosphorous acids salts, tertiary amine and imidazoline, the technology needed to place a alkyl or acyl moiety into the molecule and make the compounds of the present invention was not appreciated. It was also not until the compounds of the present invention that the concept and technology needed to incorporate the glyceryl group, which adds both to the improved biodegradation, water solubility, humectancy properties and mildness to skin and eyes.

THE INVENTION

OBJECT OF THE INVENTION

It is the object of the present invention to provide a series of novel ester based phosphobetaine compounds which are environmentally friendly, high foaming, low irritation to eyes and skin, have an inverse cloud point and are substantive to the surface of a fibers, and are very effective emulsifiers, and by virtue of their ester linkage are less persistent in the aquatic environment.

Still another object of the present invention is to provide a series of ester based phosphobetaine compounds that have differing solubilities in water and organic solvents. This is achieved by selection of the phosphate used as a raw material and the amine chosen for preparation of the phosphobetaine.

Application of the compounds of the invention can be from solvent, aqueous dispersion or solution, or applied neat in these processes.

SUMMARY OF THE INVENTION

The present invention relates to a series of novel ester based phosphobetaine compounds. The amine group typically will be a quaternized nitrogen. Hence the products are amphoteric, having both an anionic and cationic group present on the same pendant group. The glyceryl group contributes properties to these surfactants resulting in compounds that are outstanding emulsifiers, foaming intensely, are non irritating to eyes and skin and deposits on fiber surfaces and form effective surface modifying finishes. The compounds of the present invention are therefore very well suited to applications in the personal care market.

The compounds of this invention having a pendant amphoteric group, and an ester linkage are represented by the following formula;

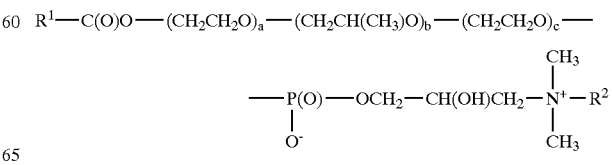

wherein

R' is alkyl or alkylene having between 7 and 21 carbon atoms;
a, b and c are each independently integers ranging from 0 to 20, with the proviso that a+b+c be equal to or greater than 1;
$R^2$ is selected from the group consisting of;
alkyl having 7 to 21 carbon atoms and $R^3$—C(O)—N(H)—(CH$_2$)$_3$—

$R^3$ is alkyl having 7 to 21 carbon atoms.

The reaction sequence needed to produce the compounds of the present invention is multi-stepped starts with the phosphation of a compound conforming to the following structure;
$R^1$—C(O)O—(CH$_2$CH$_2$O)$_a$—(CH$_2$CH(CH$_3$)O)$_b$—(CH$_2$CH$_2$O)$_c$H with polyphosphoric acid to produce:
$R^1$—C(O)O—(CH$_2$CH$_2$O)$_a$—(CH$_2$CH(CH$_3$)O)$_b$—(CH$_2$CH$_2$O)$_c$P(O)—(OH)$_2$.

The phosphation reagent used in the reaction is polyphosphoric acid, since the reaction with it results in minimal diester. In a preferred embodiment, the reaction is conducted at a mole ratio of 1 (ester) to 0.9 phosphating reagent. This molar excess of ester results in even less diester.

In a subsequent step the ester phosphate is reacted with a either a compound conforming to one of the following structures;

$$\underset{CH_2-CH-CH_2-\overset{\overset{CH_3}{|}}{\underset{\underset{CH_3}{|}}{N^+}}-R^2 \; Cl^-}{\overset{O}{\diagdown\!\diagup}} \quad \text{or}$$

$$Cl-CH_2-\underset{OH}{\overset{|}{C}}H-CH_2-\overset{\overset{CH_3}{|}}{\underset{\underset{CH_3}{|}}{N^+}}-R^2 \; Cl^-$$

to give the desired product. Both classes of products are commercially available from a variety of manufacturers including DeGussa and Siltech Corporation.

Preferred Embodiments

In a preferred embodiment $R^2$ alkyl having 7 to 21 carbon atoms.

In a preferred embodiment $R^2$ is $R^3$—C(O)—N(H)—(CH$_2$)$_3$—.

In a preferred embodiment $R^1$ is $C_7H_{17}$.
In a preferred embodiment $R^1$ is $C_9H_{19}$.
In a preferred embodiment $R^1$ is $C_{11}H_{23}$.
In a preferred embodiment $R^1$ is $C_{13}H_{27}$.
In a preferred embodiment $R^1$ is $C_{15}H_{31}$.
In a preferred embodiment $R^1$ is $C_{17}H_{35}$.
In a preferred embodiment $R^1$ is $C_{19}H_{39}$.
In a preferred embodiment $R^1$ is $C_{21}H_{43}$.

In a preferred embodiment $R^1$ is derived from a natural oil including coconut, avocado, olive, castor, borage, soybean, sunflower, safflower, cottonseed, and wheat germ oil.

EXAMPLES

Alkoxylate Esters

The alkoxylated esters used as raw materials in the preparation of the intermediate used to make the products of the present invention are articles of commerce available from Siltech LLC Dacula, Ga. and others. They conform to the following structure;

$R^1$—C(O)O—(CH$_2$CH$_2$O)$_a$—(CH$_2$CH(CH$_3$)O)$_b$—CH$_2$CH$_2$O)$_c$H wherein;

$R^1$ is alkyl or alkylene having between 7 and 21 carbon atoms;
a, b and c are each independently integers ranging from 0 to 20, with the proviso that a+b+c be equal to or greater than 1.

| Example | $R^1$ | a | b | c |
|---|---|---|---|---|
| 1 | $C_7H_{15}$ | 0 | 0 | 1 |
| 2 | $C_9H_{19}$ | 0 | 10 | 0 |
| 3 | $C_{11}H_{23}$ | 9 | 0 | 0 |
| 4 | $C_{13}H_{27}$ | 15 | 2 | 5 |
| 5 | $C_{15}H_{31}$ | 10 | 20 | 10 |
| 6 | $C_{17}H_{35}$ | 10 | 0 | 0 |
| 7 | $C_{19}H_{39}$ | 5 | 2 | 5 |
| 8 | $C_{21}H_{43}$ | 12 | 11 | 7 |
| 9 | $C_{17}H_{33}$ | 5 | 5 | 5 |
| 10 | $C_{21}H_{41}$ | 20 | 20 | 20 |

Polyphosphoric Acid

Polyphosphoric acid is an item of commerce. It is commercially available from a variety of sources. It is also called phospholeum, 115% phosphoric acid and tetraphosphoric acid. It is listed in the Merck Index.

Preparation of Ester Phosphate

The phosphation is carried out as follows: To a suitable vessel with good agitation is added the specified number of grams of specified alkoxylate ester (Example 1–10). The material is heated to 60° C. Next, add 90.0 grams of polyphosphoric acid. The polyphosphoric acid is very thick and is added slowly to insure a uniform mixture is achieved. After the mixture becomes uniform heat to 90. degree. C. The mixture will clear. Hold at 90° C. to 100° C. for 3 hours. The product is used without additional purification.

| | Alkoxylate Ester | |
|---|---|---|
| Example | Example | Grams |
| 11 | 1 | 171.1 |
| 12 | 2 | 745.0 |
| 13 | 3 | 579.0 |
| 14 | 4 | 1208.0 |
| 15 | 5 | 2299.0 |
| 16 | 6 | 707.0 |
| 17 | 7 | 853.0 |
| 18 | 8 | 1808.0 |
| 19 | 9 | 1000.0 |
| 20 | 10 | 3261.0 |

Reactive Intermediates (Examples 21–52)

(a) Epoxy Alkyl

The compound of this class conform to the following structure;

$$\underset{CH_2-CH-CH_2-\overset{\overset{CH_3}{|}}{\underset{\underset{CH_3}{|}}{N^+}}-R^2 \; Cl^-}{\overset{O}{\diagdown\!\diagup}}$$

wherein $R^2$ is alkyl having 7 to 21 carbon atoms.

| Example | $R^2$ |
|---------|-------|
| 21 | $C_7H_{17}$ |
| 22 | $C_9H_{19}$ |
| 23 | $C_{11}H_{23}$ |
| 24 | $C_{13}H_{27}$ |
| 25 | $C_{15}H_{31}$ |
| 26 | $C_{17}H_{35}$ |
| 27 | $C_{19}H_{39}$ |
| 28 | $C_{21}H_{43}$ |

Epoxy Alkylamido

The compounds of this class conform to the following structure;

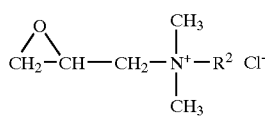

wherein $R^2$ is $R^3$—C(O)—N(H)—(CH$_2$)$_3$—and $R^3$ is alkyl having 7 to 21 carbon atoms.

| Example | $R^2$ |
|---------|-------|
| 29 | $C_7H_{17}$ |
| 30 | $C_9H_{19}$ |
| 31 | $C_{11}H_{23}$ |
| 32 | $C_{13}H_{27}$ |
| 33 | $C_{15}H_{31}$ |
| 34 | $C_{17}H_{35}$ |
| 35 | $C_{19}H_{39}$ |
| 36 | $C_{21}H_{43}$ |

(c) Chloro Alkyl

The compounds of this class conform to the following structure;

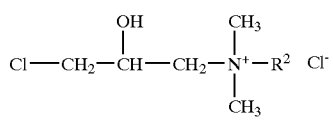

wherein $R^2$ is alkyl having 7 to 21 carbon atoms.

| Example | $R^2$ |
|---------|-------|
| 37 | $C_7H_{17}$ |
| 38 | $C_9H_{19}$ |
| 39 | $C_{11}H_{23}$ |
| 40 | $C_{13}H_{27}$ |
| 41 | $C_{15}H_{31}$ |
| 42 | $C_{17}H_{35}$ |
| 43 | $C_{19}H_{39}$ |
| 44 | $C_{21}H_{43}$ |

(d) Chloro Alkylamido

The compounds of this class conform to the following structure;

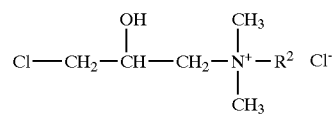

wherein $R^2$ is $R^3$—C(O)—N(H)—(CH$_2$)$_3$—. and $R^3$ alkyl having 7 to 21 carbon atoms.

| Example | $R^2$ |
|---------|-------|
| 45 | $C_7H_{17}$ |
| 46 | $C_9H_{19}$ |
| 47 | $C_{11}H_{23}$ |
| 48 | $C_{13}H_{27}$ |
| 49 | $C_{15}H_{31}$ |
| 50 | $C_{17}H_{35}$ |
| 51 | $C_{19}H_{39}$ |
| 52 | $C_{21}H_{43}$ |

Preparation of Ester Phosph Betaines

The chloro-glyceryl-phosphate (example 11–20) is reacted with the reactive intermediate (examples 21–52) in aqueous solution at a pH of between 7 and 11, with a preferred pH of 8.5–9.5 and with a preferred solids of between 30–40.

General Procedure

To the specified number of grams of water is added the specified number of grams of ester phosphate (examples 11–20) under good agitation. The pH is adjusted using 50% NaOH to 8.8. The batch is heated to 80° C. Next, add the specified number of grams of the specified reactive intermediate Example (21–52). The pH is adjusted as the reaction proceeds keeping it between 8.0 and 9.0 with the 50% NaOH. The temperature is then kept between 80–90° C. and the pH is kept between 8.0 and 9.0 for about 6–8 hours. The reaction progress is monitored by inorganic chloride concentration. The reaction is considered complete when the amount of chloride ion reaches 98% of theoretical.

| | Ester phosphate | | Reactive Intermediate | | Water |
|---------|---------|--------|---------|--------|--------|
| Example | Example | Grams | Example | Grams | Grams |
| 53 | 1 | 269.0 | 21 | 239.0 | 943.0 |
| 54 | 2 | 843.0 | 22 | 265.0 | 2058.0 |
| 55 | 3 | 677.0 | 23 | 293.0 | 1801.0 |
| 56 | 4 | 1307.0 | 24 | 321.0 | 3023.0 |
| 57 | 5 | 2397.0 | 25 | 349.0 | 5100.0 |
| 58 | 6 | 805.0 | 26 | 377.0 | 2195.0 |
| 59 | 7 | 951.0 | 27 | 405.0 | 2518.0 |
| 60 | 8 | 1906.0 | 28 | 433.0 | 4344.0 |
| 61 | 9 | 1098.0 | 29 | 324.0 | 2640.0 |
| 62 | 10 | 3359.0 | 30 | 350.0 | 6888.0 |
| 63 | 1 | 269.0 | 31 | 378.0 | 1201.0 |
| 64 | 2 | 843.0 | 32 | 406.0 | 2319.0 |
| 65 | 3 | 677.0 | 33 | 434.0 | 2063.0 |
| 66 | 4 | 1307.0 | 34 | 462.0 | 3285.0 |
| 67 | 5 | 2397.0 | 35 | 490.0 | 5361.0 |
| 68 | 6 | 805.0 | 36 | 519.0 | 2459.0 |
| 69 | 7 | 951.0 | 37 | 276.0 | 2279.0 |
| 70 | 8 | 1906.0 | 38 | 302.0 | 4100.0 |
| 71 | 9 | 1098.0 | 39 | 330.0 | 2652.0 |
| 72 | 10 | 3359.0 | 40 | 358.0 | 6903.0 |
| 73 | 1 | 269.0 | 41 | 386.0 | 1216.0 |
| 74 | 2 | 843.0 | 42 | 414.0 | 2334.0 |
| 75 | 3 | 677.0 | 43 | 442.0 | 2078.0 |
| 76 | 4 | 1307.0 | 44 | 470.0 | 3300.0 |
| 77 | 5 | 2397.0 | 45 | 361.0 | 5122.0 |

-continued

| | Ester phosphate | | Reactive Intermediate | | Water |
|---|---|---|---|---|---|
| Example | Example | Grams | Example | Grams | Grams |
| 78 | 6 | 805.0 | 46 | 387.0 | 2214.0 |
| 79 | 7 | 951.0 | 47 | 415.0 | 2537.0 |
| 80 | 8 | 1906.0 | 48 | 443.0 | 4362.0 |
| 81 | 9 | 1098.0 | 49 | 471.0 | 2914.0 |
| 82 | 10 | 3359.0 | 50 | 499.0 | 7165.0 |
| 83 | 10 | 3359.0 | 51 | 527.0 | 7216.0 |
| 84 | 9 | 1098.0 | 52 | 555.0 | 3070.0 |

Applications Examples

The compounds of the present invention are used as prepared without additional purification. They are high foaming compounds that give good conditioning effects to hair and skin. Additionally, they are non-persistent in the aquatic environment and are non-irritating to eyes and skin.

The proper selection of the compound form the present invention will result in differing amounts of conditioning. Generally as if the R group is small, the compounds are good wetting agents, as the R group gets longer the compounds become detergents. Finally, as they become very large the compounds become conditioners.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended here be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. An ester phosphobetaine conforming to the following structure;

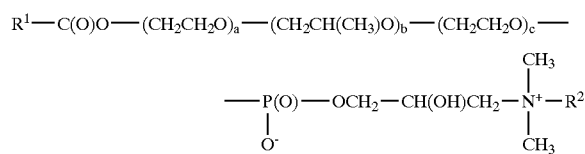

wherein;

$R^1$ is alkyl or alkylene having between 7 and 21 carbon atoms;

a, b and c are each independently integers ranging from 0 to 20, with the proviso that a+b+c be equal to or greater than 1;

$R^2$ is selected from the group consisting of;

alkyl having 7 to 21 carbon atoms and

$R^3$ is alkyl having 7 to 21 carbon atoms.

2. An ester phosphobetaine of claim 1 wherein $R^2$ alkyl having 7 to 21 carbon atoms.

3. An ester phosphobetaine of claim 1 wherein $R^2$ is $R^3$—C(O)—N(H)—(CH$_2$)$_3$—.

4. An ester phosphobetaine of claim 2 wherein $R^1$ is $C_7H_{17}$.

5. An ester phosphobetaine of claim 2 wherein $R^1$ is $C_9H_{19}$.

6. An ester phosphobetaine of claim 2 wherein $R^1$ is $C_{11}H_{23}$.

7. An ester phosphobetaine of claim 2 wherein $R^1$ is $C_{13}H_{27}$.

8. An ester phosphobetaine of claim 2 wherein $R^1$ is $C_{15}H_{31}$.

9. An ester phosphobetaine of claim 2 wherein $R^1$ is $C_{17}H_{35}$.

10. An ester phosphobetaine of claim 2 wherein $R^1$ is $C_{19}H_{39}$.

11. An ester phosphobetaine of claim 2 wherein $R^1$ is $C_{21}H_{43}$.

12. An ester phosphobetaine of claim 3 wherein $R^1$ is $C_7H_{17}$.

13. An ester phosphobetaine of claim 3 wherein $R^1$ is $C_9H_{19}$.

14. An ester phosphobetaine of claim 3 wherein $R^1$ is $C_{11}H_{23}$.

15. An ester phosphobetaine of claim 3 wherein $R^1$ is $C_{13}H_{27}$.

16. An ester phosphobetaine of claim 3 wherein $R^1$ is $C_{15}H_{31}$.

17. An ester phosphobetaine of claim 3 wherein $R^1$ is $C_{17}H_{35}$.

18. An ester phosphobetaine of claim 3 wherein $R^1$ is $C_{19}H_{39}$.

19. An ester phosphobetaine of claim 3 wherein $R^1$ is $C_{21}H_{43}$.

* * * * *